US007365215B2

(12) United States Patent
Nishino et al.

(10) Patent No.: US 7,365,215 B2
(45) Date of Patent: Apr. 29, 2008

(54) PROCESS FOR PREPARING 4-AMINOTETRAHYDROPYRAN COMPOUND AND AN ACID SALT THEREOF, SYNTHETIC INTERMEDIATE THEREOF AND PROCESS FOR PREPARING THE SAME

(75) Inventors: Shigeyoshi Nishino, Ube (JP); Kenji Hirotsu, Ube (JP); Hidetaka Shima, Ube (JP); Keiji Iwamoto, Ube (JP); Takashi Harada, Ube (JP); Shinobu Suzuki, Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 82 days.

(21) Appl. No.: 10/564,709

(22) PCT Filed: Jul. 14, 2004

(86) PCT No.: PCT/JP2004/010010

§ 371 (c)(1),
(2), (4) Date: Jan. 13, 2006

(87) PCT Pub. No.: WO2005/005406

PCT Pub. Date: Jan. 20, 2005

(65) Prior Publication Data
US 2007/0106083 A1 May 10, 2007

(30) Foreign Application Priority Data

| Jul. 14, 2003 | (JP) | ............................. 2003-196229 |
| Aug. 7, 2003 | (JP) | ............................. 2003-288324 |
| Aug. 25, 2003 | (JP) | ............................. 2003-300129 |
| Oct. 1, 2003 | (JP) | ............................. 2003-342771 |
| Mar. 19, 2004 | (JP) | ............................. 2004-079883 |

(51) Int. Cl.
*C07D 315/00* (2006.01)
(52) U.S. Cl. .................................................. 549/419
(58) Field of Classification Search ................. 549/419
See application file for complete search history.

(56) References Cited

U.S. PATENT DOCUMENTS

| 5,866,588 A | 2/1999 | Ayscough et al. |
| 5,965,575 A | 10/1999 | Peglion et al. |
| 6,103,718 A | 8/2000 | Sterk |
| 6,653,489 B2 | 11/2003 | Harada et al. |

FOREIGN PATENT DOCUMENTS

| EP | 0 885 890 A1 | 12/1998 |
| JP | 63-48548 A | 3/1988 |
| JP | 63-48550 A | 3/1988 |
| JP | 10-7658 A | 1/1998 |
| JP | 10-279578 A | 10/1998 |
| JP | 11-510180 A | 7/1999 |
| JP | 11-510180 A | 9/1999 |
| JP | 2001-508078 A | 6/2001 |
| JP | 2004-250340 A | 9/2004 |
| WO | WO-97/06167 A1 | 2/1997 |
| WO | WO-01/42232 A1 | 6/2001 |

OTHER PUBLICATIONS

Van der Mey et al., Journal of Medicinal Chemistry, 2002, vol. 45, pp. 2520-2525.*
Natio et al., The Journal of Antibiotics, 1974, pp. 838-850.*
Allegretti, M. et al., Tetrahedron Letters, 2001, vol. 42, No. 25, pp. 4257-4259.

* cited by examiner

*Primary Examiner*—Margaret D. Seaman
*Assistant Examiner*—Niloofar Rahmani
(74) *Attorney, Agent, or Firm*—Birch, Stewart, Kolasch & Birch, LLP

(57) ABSTRACT

The present invention relates to a process for preparing 4-aminotetrahydropyran compound and an acid salt thereof represented by the formula (1):

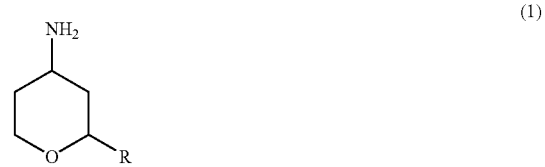

wherein R represents a hydrogen atom or a hydrocarbon group,
which comprises subjecting a 4-hydrazinotetrahydropyran compound or an acid salt thereof represented by the formula (2):

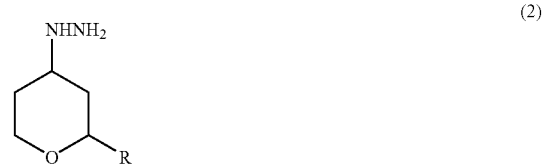

wherein R has the same meaning as defined above,
to decomposition reaction in the presence of at least one compound selected from Raney nickel, a noble metal catalyst and a metal oxide, and a synthetic intermediate thereof and a process for preparing the same.

12 Claims, No Drawings

PROCESS FOR PREPARING 4-AMINOTETRAHYDROPYRAN COMPOUND AND AN ACID SALT THEREOF, SYNTHETIC INTERMEDIATE THEREOF AND PROCESS FOR PREPARING THE SAME

TECHNICAL FIELD

The present invention relates to a novel process for preparing a 4-aminotetrahydropyran compound and an acid salt thereof. The 4-aminotetrahydropyran compound and an acid salt thereof are useful compounds as a synthetic starting material for medicine, agricultural chemicals, etc. The present invention also relates to a 2-substituted tetrahydropyranyl-4-sulfonate and a process for preparing the same. The 2-substituted tetrahydropyranyl-4-sulfonate is a compound which is useful as a synthetic intermediate for medicine and agricultural chemicals, etc.

BACKGROUND ART

As a method for preparing a 4-aminotetrahydropyran compound and an acid salt thereof, it has conventionally been disclosed a method in which tetrahydropyran-4-one, ammonium acetate, molecular sieve powder and sodium cyanoborohydride are reacted in ethanol to give a 4-aminotetrahydropyran with yield of 12% (see, for example, Japanese PCT Laid-Open Publication Hei.11-510180 (pages 66 to 67)). However, according to this method, there are problems that a markedly excessive amount of ammonia source (for example, ammonium acetate) must be used, and also, a reaction system is complicated so that operations for the reaction are troublesome and yield of the objective product is low.

Also, with regard to 2-substituted tetrahydropyranyl-4-sulfonate which can be used as a synthetic starting material for the above-mentioned compound and a process for preparing the same have never been known.

An object of the present invention is to provide an industrially suitable process for preparing a 4-aminotetrahydropyran compound and an acid salt thereof which does not require complicated operations and can prepare a 4-aminotetrahydropyran compound and an acid salt thereof with a simple and easy method.

Another object of the present invention is to provide an industrially suitable 2-substituted tetrahydropyranyl-4-sulfonate and a process for preparing the same which can solve the above-mentioned problems, and can prepare the 2-substituted tetrahydropyranyl-4-sulfonate under mild conditions with a simple and easy method and a high yield.

DISCLOSURE OF THE INVENTION

The present invention relates to a process for preparing a 4-aminotetrahydropyran compound represented by the formula (1):

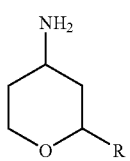

(1)

wherein R represents a hydrogen atom or a hydrocarbon group, or an acid salt thereof, which comprises subjecting a 4-hydrazinotetrahydropyran compound represented by the formula (2):

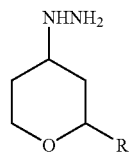

(2)

wherein R has the same meaning as defined above, or an acid salt thereof to decomposition reaction in the presence of at least one compound selected from Raney nickel, a noble metal catalyst and a metal oxide.

The present invention also relates to a process for preparing the 4-aminotetrahydropyran compound or an acid salt thereof, which comprises (A) the first step of reacting a 4-substituted tetrahydropyran compound represented by the formula (3):

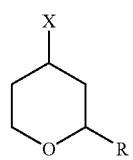

(3)

wherein R has the same meaning as defined above, and X represents a leaving group, with a hydrazine to prepare a 4-hydrazinotetrahydropyran compound represented by the formula (2):

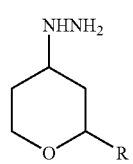

(2)

wherein R has the same meaning as defined above, or an acid salt thereof, (B) then, the second step of decomposing the 4-hydrazinotetrahydropyran compound or an acid salt thereof in the reaction mixture in the presence of at least one compound selected from Raney nickel, a noble metal catalyst and a metal oxide to prepare a 4-aminotetrahydropyran compound represented by the formula (1):

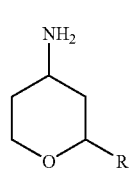

(1)

wherein R has the same meaning as defined above.

The present invention also relates to a 2-substituted 4-hydrazinotetrahydropyran compound represented by the above-mentioned formula (2):

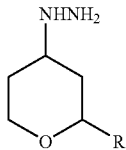

(2)

wherein R has the same meaning as defined above, or an acid salt thereof.

The present invention further relates to a 2-substituted tetrahydropyranyl-4-sulfonate represented by the formula (4):

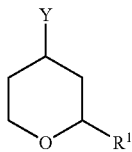

(4)

wherein $R^1$ represents a hydrocarbon group, and Y represents a sulfonyloxy group.

The present invention also relates to a process for preparing the 2-substituted tetrahydropyranyl-4-sulfonate represented by the above-mentioned formula (4) which comprises reacting 3-buten-1-ol with an aldehyde compound represented by the formula (5):

$R^1CHO$ (5)

wherein $R^1$ has the same meaning as defined above, a polymer thereof or an acetal compound thereof, and an organic sulfonic acid.

BEST MODE TO CARRY OUT THE INVENTION

The 4-hydrazinotetrahydropyran compound to be used in the preparation process of the 4-aminotetrahydropyran compound of the present invention is represented by the above-mentioned formula (2). In the formula (2), R represents a hydrogen atom or a hydrocarbon group, and as the hydrocarbon group, there may be mentioned, for example, an alkyl group such as a methyl group, an ethyl group, a propyl group, a butyl group, a pentyl group, a hexyl group, etc.; a cycloalkyl group such as a cyclopropyl group, a cyclobutyl group, a cyclopentyl group, a cyclohexyl group, etc.; an aralkyl group such as a benzyl group, a phenethyl group, etc.; an aryl group such as a phenyl group, a tolyl group, a naphthyl group, an anthryl group, etc. Incidentally, these groups may include various kinds of isomers. In the present invention, of these, as R, a hydrogen atom, a methyl group, an ethyl group or a phenyl group is preferred.

As the above-mentioned acid salt of the 4-hydrazinotetrahydropyran compound, there may be mentioned a salt of an inorganic acid such as hydrogen chloride, hydrogen bromide, hydrogen iodide, hydrogen fluoride, sulfuric acid, hydrogen nitrate, etc., a salt of an organic acid such as formic acid, acetic acid, propionic acid, oxalic acid, succinic acid, maleic acid, salicylic acid, methanesulfonic acid, ethanesulfonic acid, trifluoromethanesulfonic acid, benzenesulfonic acid, p-toluenesulfonic acid, p-chlorobenzenesulfonic acid, p-bromobenzenesulfonic acid, phthalic acid, isophthalic acid, benzoic acid, etc.

Such a 4-hydrazinotetrahydropyran compound may be mentioned, for example, 4-hydrazinotetrahydropyran, 4hydrazino-2-methyltetrahydropyran, 4-hydrazino-2-ethyltetrahydropyran, 4-hydrazino-2-n-propyltetrahydropyran, 4hydrazino-2-phenyltetrahydropyran, etc. Also, as a salt thereof, there may be mentioned a salt of the abovementioned acids, preferably hydrochloride, hydrobromide, sulfate, formate, methanesulfonate, p-toluenesulfonate, etc.

The Raney nickel to be used in the decomposition reaction of the present invention is an alloy comprising nickel and aluminum as main components, and that preferably containing a nickel content of 10 to 90% by weight, more preferably 40 to 80% by weight is used. In general, developed Raney nickel is used, and a Raney nickel which has been subjected to pretreatment according to the various methods or a stabilized Raney nickel may be also used. Further, that in which a metal such as cobalt, iron, lead, chromium, titanium, molybdenum, vanadium, manganese, tin, tungsten, etc. is/are contained in a Raney nickel may be also used.

An amount of the above-mentioned Raney nickel to be used is, in terms of a nickel atom, preferably 0.01 to 1.0 g, more preferably 0.1 to 0.5 g based on 1 g of the 4-hydrazinotetrahydropyran compound or an acid salt thereof.

The noble metal catalyst to be used in the decomposition reaction of the present invention is a catalyst containing at least one of palladium and platinum, and there may be specifically mentioned, for example, palladium/carbon, palladium/barium sulfate, palladium hydroxide/carbon, platinum/carbon, platinum sulfate/carbon, palladium-platinum/carbon, etc., preferably palladium/carbon, platinum/carbon is/are used. Incidentally, these noble metal catalysts may be used alone or in combination of two or more in admixture.

An amount of the above-mentioned noble metal catalyst to be used is, in terms of a metal atom, preferably 0.00025 to 0.5 g, more preferably 0.0005 to 0.025 g based on 1 g of the 4-hydrazinotetrahydropyran compound or an acid salt thereof.

The metal oxide to be used in the decomposition reaction of the present invention includes various kinds of oxides of a metal, and it is not specifically limited so long as the objects of the present invention have been accomplished. As such a metal oxide, copper (I) oxide or copper (II) oxide is preferably used. Incidentally, the metal oxide may be used alone or in combination of two or more in admixture.

An amount of the above-mentioned metal oxide to be used is preferably 0.00025 to 0.5 g, more preferably 0.0005 to 0.025 g based on 1 g of the 4-hydrazinotetrahydropyran compound or an acid salt thereof.

The decomposition reaction of the present invention is preferably carried out in a solvent. As the solvent to be used, it is not specifically limited so long as it does not inhibit the reaction, and there may be mentioned, for example, water; an alcohol such as methanol, ethanol, n-propyl alcohol, isopropyl alcohol, n-butyl alcohol, sec-butyl alcohol, t-butyl alcohol, etc.; an aromatic hydrocarbon carbon such as benzene, toluene, xylene, mesitylene, etc.; a halogenated aliphatic hydrocarbon such as chloroform, dichloroethane, etc.; an ether such as diethyl ether, tetrahydrofuran, diisopropyl ether, etc., preferably water, an alcohol, more preferably water, methanol, ethanol, isopropyl alcohol is/are used.

Incidentally, these organic solvents may be used alone or in combination of two or more in admixture.

An amount of the above-mentioned solvent is optionally controlled depending on a degree of uniformity or condition of stirring of the reaction solution, and is preferably 0.1 to 100 ml, more preferably 1.0 to 10 ml based on 1 g of the 4-hydrazinotetrahydropyran compound.

Also, in the decomposition reaction of the present invention, it is desired to exist a hydrogen gas in a system so that a reaction rate is heightened or a reaction yield of the objective product is heightened.

The decomposition reaction of the present invention is carried out, for example, by the method that the 4-hydrazinotetrahydropyran compound or an acid salt thereof, at least one compound selected from Raney nickel, the noble metal catalyst and metal oxide and a solvent are mixed and reacted with stirring, and the like. A reaction temperature at the time is preferably 20 to 120° C., more preferably 50 to 100° C., and a reaction pressure is not specifically limited, and preferably 0.1 to 5 MPa, more preferably 0.1 to 2 MPa. Also, a reaction time may be any time so long as the reaction has been completed and it is not specifically limited.

Incidentally, the final product, the 4-aminotetrahydropyran compound and an acid salt thereof, can be isolated and purified after completion of the reaction by general methods, for example, filtration, concentration, distillation, recrystallization, column chromatography, etc. Incidentally, the Raney nickel in the reaction solution is desirably removed by using amines such as triethylamine, tetraethylenepentamine, pentaethylenehexamine, etc., after completion of the reaction.

As the 4-aminotetrahydropyran compound obtained by the decomposition reaction as mentioned above, there may be mentioned, for example, 4-aminotetrahydropyran, 4-amino-2-methyltetrahydropyran, 4-amino-2-ethyltetrahydropyran, 4-amino-2-n-propyltetrahydropyran, 4-amino-2-phenyltetrahydropyran, etc. Also, as a salt thereof, there may be mentioned a salt of the above-mentioned acids, and preferably mentioned a hydrochloride, hydrobromide, sulfate, formate, methanesulfonate, p-toluenesulfonate, etc.

The 4-hydrazinotetrahydropyran compound represented by the formula (2) to be used in the above-mentioned decomposition reaction can be prepared according to the following (A) the first step.

(A) First Step

The first step of the present invention is a step of obtaining a reaction solution comprising a 4-hydrazinotetrahydropyran compound or an acid salt thereof as a main product by reacting the 4-substituted tetrahydropyran compound with a hydrazine.

The 4-substituted tetrahydropyran compound to be used in the first step of the present invention is represented by the above-mentioned formula (3). In the formula (3), R has the same meaning as defined above.

Also, X is a leaving group, and there may be mentioned, for example, a halogen atom such as a fluorine atom, a chlorine atom, a bromine atom, an iodine atom, etc.; an alkylsulfonyloxy group such as a methanesulfonyloxy group, an ethanesulfonyloxy group, a 1-propenesulfonyloxy group, a 2-propanesulfonyloxy group, etc.; an arylsulfonyloxy group such as a benzenesulfonyloxy group, a p-toluenesulfonyloxy group, a 2,4,6-trimethylbenzenesulfonyloxy group, a 2,4,6-triisopropylbenzenesulfonyloxy group, a 1-naphthalenesulfonyloxy group, a 2-naphthalenesulfonyloxy group, a p-methoxybenzenesulfonyloxy group, a p-chlorobenzenesulfonyloxy group, an o-nitrobenzenesulfonyloxy group, etc., preferably an alkylsulfonyloxy group, an arylsulfonyloxy group, more preferably a methanesulfonyloxy group, a p-toluenesulfonyloxy group.

An amount of the hydrazine to be used in the first step of the present invention is preferably 1.0 to 20.0 mol, more preferably 4.0 to 15.0 mol based on 1 mol of the 4-substituted tetrahydropyran compound. Incidentally, the hydrazine may be used in any forms such as an anhydride (free hydrazine), a hydrate or an acid salt (including that the acid salt is neutralized with a base), or an aqueous solution, etc.

The first step of the present invention is preferably carried out in a solvent. As the solvent to be used, it is not specifically limited so long as it does not inhibit the reaction, and there may be mentioned, for example, water, an alcohol such as methanol, ethanol, n-propyl alcohol, isopropyl alcohol, n-butyl alcohol, sec-butyl alcohol, t-butyl alcohol, etc.; an aromatic hydrocarbon such as benzene, toluene, xylene, mesitylene, etc.; a halogenated aliphatic hydrocarbon such as chloroform, dichloroethane, etc.; an ether such as diethyl ether, tetrahydrofuran, diisopropyl ether, etc., preferably water, an alcohol, more preferably water, methanol, ethanol, isopropyl alcohol is/are used. Incidentally, these organic solvents may be used alone or in combination of two or more in admixture.

An amount of the above-mentioned solvent to be used is optionally controlled depending on a degree of uniformity or condition of stirring of the reaction solution, and is preferably 0.1 to 50 ml, more preferably 0.5 to 10 ml based on 1 g of the 4-substituted tetrahydropyran compound.

The first step of the present invention is carried out, for example, by the method in which the 4-substituted tetrahydropyran compound, a hydrazine and an organic solvent are mixed in an inert gas atmosphere, and reacted with stirring, etc. A reaction temperature at the time is preferably 20 to 120° C., more preferably 50 to 100° C., and a reaction pressure is not specifically limited. Also, a reaction time may be any time so long as the reaction has been completed and it is not specifically limited.

Incidentally, according to the first step, a reaction solution comprising the 4-hydrazinotetrahydropyran compound or an acid salt thereof as a main product can be obtained, and the reaction solution can be used in the subsequent (B) second step as such or after adjusting an amount thereof.

(B) Second Step

The second step can be carried out in the same manner as in the decomposition reaction of the above-mentioned 4-hydrazinotetrahydropyran compound to the 4-aminotetrahydropyran compound.

The 2-substituted tetrahydropyran-4-sulfonate to be used as the starting material in the above-mentioned first step of the present invention is represented by the above-mentioned formula (4). In the formula (4), $R^1$ is a hydrocarbon group, and as the hydrocarbon group, there may be mentioned the same hydrocarbon group of R in the above-mentioned formula (1), and there may be mentioned, for example, an alkyl group such as a methyl group, an ethyl group, a propyl group, a butyl group, a pentyl group, a hexyl group, etc.; a cycloalkyl group such as a cyclopropyl group, a cyclobutyl group, a cyclopentyl group, a cyclohexyl group, etc.; an aralkyl group such as a benzyl group, a phenethyl group, etc.; an aryl group such as a phenyl group, a tolyl group, a naphthyl group, an anthryl group, etc. Incidentally, these groups include various kinds of isomers. In the present invention, of these, a methyl group, an ethyl group or a phenyl group is preferably mentioned as $R^1$.

Y is a sulfonyloxy group, and there may be mentioned, for example, an alkylsulfonyloxy groups such as a methanesulfonyloxy group, an ethanesulfonyloxy group, a trifluoromethanesulfonyloxy group, etc.; an arylsulfonyloxy group such as a benzenesulfonyloxy group, a p-toluenesulfonyloxy group, a p-chlorobenzenesulfonyloxy group, a p-bromobenzenesulfonyloxy group, etc.

As the 2-substituted tetrahydropyran-4-sulfonate represented by the formula (4), there may be mentioned, for example, 2-methyltetrahydropyran-4-methanesulfonate, 2-methyltetrahydropyran-4-ethanesulfonate, 2-methyltetrahydropyran-4-trifluoromethanesulfonate, 2-methyltetrahydropyran-4-benzenesulfonate, 2-methyltetrahydropyran-4-p-toluenesulfonate, 2-methyltetrahydropyran-4-p-chloroben-zenesulfonate, 2-methyltetrahydropyran-4-p-bromobenzene-sulfonate, 2-ethyltetrahydropyran-4-methanesulfonate, 2-ethyltetrahydropyran-4-ethanesulfonate, 2-ethyltetrahydro-pyran-4-trifluoromethanesulfonate, 2-ethyltetrahydropyran-4-benzenesulfonate, 2-ethyltetrahydropyran-4-p-toluenesulfonate, 2-ethyltetrahydropyran-4-p-chlorobenzenesulfonate, 2-ethyltetrahydropyran-4-p-bromobenzenesulfonate, 2-phenyltetrahydropyran-4-methanesulfonate, 2-phenyltetra-hydropyran-4-ethanesulfonate, 2-phenyltetrahydropyran-4-trifluoromethanesulfonate, 2-phenyltetrahydropyran-4-benzenesulfonate, 2-phenyltetrahydropyran-4-p-toluenesulfonate, 2-phenyltetrahydropyran-4-p-chlorobenzenesulfonate, 2-phenyltetrahydropyran-4-p-bromobenzenesulfonate, etc.

The aldehyde compound, the polymer thereof or the acetal compound thereof to be used in the reaction of the present invention is represented by the above-mentioned formula (5). In the formula (5), $R^1$ has the same meaning as mentioned above. As such an aldehyde compound, there may be mentioned, for example, an alkyl aldehyde such as acetaldehyde, propionaldehyde, butylaldehyde, isobutyl aldehyde, valeraldehyde, isovaleraldehyde, etc., and an aryl aldehyde such as benzaldehyde, o-tolulaldehyde, m-tolulaldehyde, p-tolulaldehyde, etc. Also, as the polymer of the above-mentioned aldehyde compound, there may be mentioned, for example, paraldehyde, metaldehyde, parapropionaldehyde, etc., and as the acetal compound, there may be mentioned, for example, acetaldehyde dimethylacetal, acetaldehyde diethylacetal, etc.

An amount of the above-mentioned aldehyde compound, the polymer thereof or the acetal compound thereof is, in terms of an amount of the aldehyde, preferably 1.0 to 5.0 mol, more preferably 1.1 to 2.0 mol based on 1 mol of the 3-buten-1-ol.

As the organic sulfonic acid to be used in the reaction of the present invention, there may be mentioned, for example, an alkylsulfonic acid such as methanesulfonic acid, ethanesulfonic acid, trifluoromethanesulfonic acid, etc.; and an arylsulfonic acid such as benzenesulfonic acid, p-toluenesulfonic acid, p-chlorobenzenesulfonic acid, p-bromobenzenesulfonic acid, etc.

An amount of the above-mentioned organic sulfonic acid to be used is preferably 1.0 to 5.0 mol, more preferably 1.1 to 2.0 mol based on 1 mol of the 3-buten-1-ol.

The reaction of the present invention is desirably carried out in the presence of an organic solvent. As the organic solvent to be used, it is not specifically limited so long as it does not inhibit the reaction, and there may be mentioned, for example, an aromatic hydrocarbon such as benzene, toluene, xylene, mesitylene, etc.; a halogenated aliphatic hydrocarbon such as chloroform, dichloroethane, etc.; a carboxylic acid ester such as ethyl acetate, propyl acetate, butyl acetate, etc.; an ether such as tetrahydrofuran, dimethoxyethane, diisopropyl ether, etc.; a nitrile such as acetonitrile, propionitrile, etc., preferably used are an aromatic hydrocarbon, an ether, a carboxylic acid ester, more preferably an aromatic hydrocarbon. These organic solvents may be used alone or in combination of two or more in admixture.

An amount of the above-mentioned organic solvent to be used may be optionally controlled depending on a degree of uniformity or condition of stirring of the reaction solution, and it is preferably 0.1 to 50 ml, more preferably 0.1 to 10 ml based on 1 g of 3-buten-1-ol.

The reaction of the present invention can be carried out, for example, by the method in which 3-buten-1-ol, an aldehyde compound, an organic sulfonic acid and an organic solvent are mixed, and reacted with stirring, etc. A reaction temperature at the time is preferably 10 to 80° C., more preferably 20 to 60° C., and a reaction pressure is not specifically limited. Also, a reaction time may be any time so long as the reaction has been completed and it is not specifically limited.

Incidentally, the final product, 2-substituted tetrahydropyran-4-sulfonate can be isolated and purified after completion of the reaction by general methods including, for example, filtration, concentration, distillation, recrystallization, column chromatography, etc.

EXAMPLES

Next, the present invention will be explained in more detail by referring to Examples, but the scope of the present invention is not limited by these examples.

Reference example 1

Synthesis of 4-hydrazinotetrahydropyran

To a flask having an inner volume of 1000 ml, made of glass and equipped with a stirring device, a thermometer and a reflux condenser were charged 134.7 g (710 mmol) of tetrahydropyranyl-4-methanesulfonate with a purity of 95%, 256 ml (5.27 mol) of hydrazine monohydrate and 256 ml of ethanol, and the mixture was reacted at 70 to 80° C. for 3 hours under nitrogen atmosphere with stirring. After completion of the reaction, the reaction mixture was cooled to room temperature, 98 ml (784 mmol) of 8 mol/l aqueous sodium hydroxide solution was added to the mixture, and the resulting mixture was concentrated under reduced pressure. After adding 500 ml of toluene to the concentrate, the mixture was filtered, and the filtrate was again concentrated under reduced pressure. Precipitated solid was removed by filtration to obtain 45.0 g (Isolation yield: 51%) of 4-hydrazinotetrahydropyran with a purity of 93% (areal percentage by gas chromatography) as yellowish liquid.

Physical properties of the 4-hydrazinotetrahydropyran are as follows.

CI-MS(m/e); 117 (M+1)

$^1$H-NMR (CDCl$_3$, δ (ppm)); 1.28 to 1.41 (2H, m), 1.84 to 1.90 (2H, m), 2.69 to 2.78 (1H, m), 3.40 to 3.45 (2H, m), 3.92 to 3.98 (2H, m), 4.80 (3H, brs)

Example 1

Synthesis of 4-aminotetrahydropyran

To a flask having an inner volume of 30 ml, made of glass and equipped with a stirring device, a thermometer and a reflux condenser were charged 260 mg (2.08 mmol) of 4-hydrazinotetrahydropyran with a purity of 93% synthesized in the same manner as in the above-mentioned Reference example 1, 92 mg of developed Raney nickel and 2.5 ml of ethanol, and the mixture was reacted at 75° C. for 6 hours under hydrogen atmosphere. After completion of the reaction, the reaction mixture was cooled to room temperature and filtered, and the filtrate was analyzed (internal standard method) by gas chromatography, 136 mg (Reaction yield: 65%) of 4-aminotetrahydropyran was found to be formed.

Reference example 2

Synthesis of 4-hydrazinotetrahydropyran hydrochloride

To a flask having an inner volume of 200 ml, made of glass and equipped with a stirring device, a thermometer and a reflux condenser were charged 10.0 g (53 mmol) of tetrahydropyranyl-4-methanesulfonate with a purity of 95%, 26 ml (536 mmol) of hydrazine monohydrate and 26 ml of ethanol, and the mixture was reacted at 75° C. for 3 hours under nitrogen atmosphere with stirring. After completion of the reaction, the reaction mixture was cooled to room temperature, 14 g (72.6 mmol) of 28% by weight sodium methoxide-methanol solution was added to the mixture, and the resulting mixture was concentrated under reduced pressure. After adding 50 ml of toluene to the concentrate, the mixture was filtered and the filtrate was again concentrated under reduced pressure. The concentrate was cooled to 0° C., 50 ml of methanol and 6.5 ml (78 mmol) of 12 mol/l hydrochloric acid were added thereto, and the mixture was concentrated under reduced pressure. The concentrate was recrystallized from ethanol and toluene to obtain 2.8 g (Isolation yield: 34%) of 4-hydrazinotetrahydropyran hydrochloride with a purity of 99% (areal percentage by gas chromatography) as colorless crystals.

Physical properties of the 4-hydrazinotetrahydropyran hydrochloride are as follows.

CI-MS (m/e); 117 (M+1-HCl)

$^1$H-NMR (DMSO-$d_6$, δ (ppm)); 1.50 (2H, brs), 1.90 (2H, d, J=8.1 Hz), 3.13 (1H, brs), 3.28 (2H, dt, J=12.0, 2.4 Hz), 3.88 (2H, d, J=12.0 Hz), 4.98 (1H, brs), 10.23 (3H, brs)

Example 2

Synthesis of 4-aminotetrahydropyran hydrochloride

To a flask having an inner volume of 500 ml, made of glass and equipped with a stirring device, a thermometer and a reflux condenser were charged 60.0 g (389 mmol) of 4-hydrazinotetrahydropyran hydrochloride with a purity of 99% and synthesized in the same manner as in the above-mentioned Reference example 2, 12.0 g of a developed Raney nickel, 120 ml of ethanol and 120 ml of water, and the mixture was reacted at 750° C. for 24 hours under hydrogen atmosphere. After completion of the reaction, the reaction mixture was cooled to room temperature and filtered, and the filtrate was concentrated under reduced pressure. Then, 200 ml of n-butyl alcohol and 50 ml (600 mmol) of 12 mol/l hydrochloric acid were added to the concentrate, and the mixture was concentrated under reduced pressure to obtain 38.5 g (Isolation yield: 70%) of 4-aminotetrahydropyran hydrochloride with a purity of 98% (areal percentage by gas chromatography) as white crystals.

Physical properties of the 4-aminotetrahydropyran hydrochloride are as follows.

CI-MS (m/e); 102 (M+1-HCl)

$^1$H-NMR (DMSO-$d_6$, δ (ppm)); 1.52 to 1.66 (2H, m), 1.84 to 1.90 (2H, m), 3.15 to 3.45 (3H, m), 3.84 to 3.89 (2H, m), 8.38 (3H, brs)

Example 3

Synthesis of 4-aminotetrahydropyran

To a flask having an inner volume of 50 ml, made of glass and equipped with a stirring device, a thermometer and a reflux condenser were charged 1.0 g (6.49 mmol) of 4-hydrazinotetrahydropyran hydrochloride with a purity of 99% and synthesized in the same manner as in Reference Example 2, 200 mg of developed Raney nickel and 5 ml of ethanol, and the mixture was reacted at 75° C. for 20 hours under argon atmosphere. After completion of the reaction, the reaction mixture was cooled to room temperature and filtered, and when the filtrate was-analyzed (internal standard method) by gas chromatography, 246 mg (Reaction yield: 37%) of 4-amino-tetrahydropyran was found to be formed.

Example 4

(1) Synthesis of 4-hydrazino-2-methyltetrahydropyran hydrochloride

To a flask having an inner volume of 200 ml, made of glass and equipped with a stirring device, a thermometer and a reflux condenser were charged 10.0 g (41.2 mmol) of 2-methyltetrahydropyranyl-4-methanesulfonate with a purity of 80% and synthesized in the same manner as in the following mentioned Example 16, 20 ml (412 mmol) of hydrazine monohydrate and 20 ml of ethanol, and the mixture was reacted at 75° C. for 3 hours under nitrogen atmosphere with stirring. After completion of the reaction, the reaction mixture was cooled to room temperature, 9.45 g (49 mmol) of 28% by weight sodium methoxide-methanol solution was added to the mixture, and the resulting mixture was concentrated under reduced pressure. After adding 200 ml of toluene to the concentrate, the mixture was filtered, and the filtrate was again concentrated under reduced pressure. The concentrate was cooled to 0° C., 50 ml of methanol and 5.0 ml (60 mmol) of 12 mol/l hydrochloric acid were added to the concentrate, and then, the mixture was concentrated under reduced pressure. The concentrate was recrystallized from ethanol and toluene to obtain 3.82 g (Isolation yield: 55%) of 4-hydrazino-2-methyltetrahydropyran hydrochloride with a purity of 99% (areal percentage by gas chromatography) as colorless crystals.

Physical properties of the 4-hydrazino-2-methyltetrahydropyran hydrochloride are as follows.

Melting point; 144 to 146° C.

CI-MS (m/e); 131 (M+1-HCl)

$^1$H-NMR(DMSO-$d_6$, δ (ppm)); 1.04 (3H, d, J=6.3 Hz), 1.36 to 1.46 (1H, m), 1.67 to 1.73 (2H, m), 1.83 (1H, d, J=14.1 Hz), 3.33 to 3.36 (1H, m), 3.54 to 3.80 (3H, m), 7.70 (4H, brs)

(2) Synthesis of 4-amino-2-methyltetrahydropyran hydrochloride

To a flask having an inner volume of 500 ml, made of glass and equipped with a stirring device, a thermometer and a reflux condenser were charged 65.3 g (392 mmol) of 4-hydrazino-2-methyltetrahydropyran hydrochloride with a purity of 100% and synthesized in the same manner as in the above-mentioned (1), 18.0 g of developed Raney nickel, 120 ml of ethanol, 120 ml of water and 40 ml (320 mmol) of 8 mol/l aqueous sodium hydroxide solution, and the mixture was reacted at 75° C. for 24 hours under hydrogen atmosphere. After completion of the reaction, the reaction mixture was cooled to room temperature and filtered, and the filtrate was concentrated under reduced pressure. Then, 200 ml of n-butyl alcohol and 50 ml (600 mmol) of 12 mol/l hydrochloric acid were added to the concentrate, the resulting mixture was concentrated under reduced pressure to obtain 38.2 g (Isolation yield: 63%) of 4-amino-2-methyltetrahydropyran hydrochloride with a purity of 98% (areal percentage by gas chromatography) as white powder.

Physical properties of the 4-amino-2-methyltetrahydropyran hydrochloride are as follows.

CI-MS (m/e); 117 (M+1-HCl)

$^1$H-NMR (DMSO-$d_6$, δ (ppm)); 1.09 (3H, d, J=6.0 Hz), 1.48 to 1.84 (4H, m), 3.47 to 3.93 (4H, m), 8.44 (3H, brs)

Example 5

Synthesis of 4-amino-2-methyltetrahydropyran

To a flask having an inner volume of 100 ml, made of glass and equipped with a stirring device, a thermometer and a reflux condenser were charged 1.0 g (6.00 mmol) of 4-hydrazino-2-methyltetrahydropyran hydrochloride with a purity of 100% and synthesized in the same manner as in Example 4(1), 100 mg of developed Raney nickel, 3.0 ml (6.0 mmol) of 2 mol/l an aqueous sodium hydroxide solution and 2.5 ml of ethanol, and the mixture was reacted at 75° C. for 2 hours under hydrogen atmosphere. After completion of the reaction, the reaction mixture was cooled to room temperature and filtered, and when the filtrate was analyzed (internal standard method) by gas chromatography, 559 mg (Reaction yield: 81%) of 4-amino-2-methyltetrahydropyran was found to be formed.

Example 6

Synthesis of 4-aminotetrahydropyran hydrochloride

To a flask having an inner volume of 300 ml, made of glass and equipped with a stirring device, a thermometer and a reflux condenser were charged 30.0 g (194.6 mmol) of 4-hydrazinotetrahydropyran hydrochloride with a purity of 99% and synthesized in the same manner as in Reference example 2, 3.0 g (0.70 mmol calculated as palladium atom) of 5% by weight palladium/carbon (50% wet product) and 150 ml of ethanol, and the mixture was reacted at 75° C. for 24 hours under hydrogen atmosphere (0.1 MPa. After completion of the reaction, the reaction mixture was cooled to room temperature and filtered, and the filtrate was concentrated under reduced pressure. When the concentrate was analyzed (internal standard method) by gas chromatography, 15.9 g (Reaction yield: 81%) of 4-aminotetrahydropyran was found to be formed. Then, 200 ml of n-butyl alcohol and 17.4 g (174 mmol) of 12 mol/l hydrochloric acid were added to the concentrate, and the mixture was concentrated under reduced pressure to obtain 14.3 g (Isolation yield: 52%) of 4-aminotetrahydropyran hydrochloride with a purity of 98% (areal percentage by gas chromatography) as white crystals.

Physical properties of the 4-aminotetrahydropyran hydrochloride were the same as those in Example 2

Example 7

Synthesis of 4-aminotetrahydropyran hydrobromide

To a flask having an inner volume of 300 ml, made of glass and equipped with a stirring device, a thermometer and a reflux condenser were charged 30.0 g (194.6 mmol) of 4-hydrazinotetrahydropyran hydrochloride with a purity of 99% and synthesized in the same manner as in Reference example 2, 1.5 g (0.70 mmol calculated as palladium atom) of 10% by weight palladium/carbon (50% wet product) and 150 ml of ethanol, and the mixture was reacted at 75° C. for 24 hours under hydrogen atmosphere (0.1 MPa). After completion of the reaction, the reaction mixture was cooled to room temperature and filtered, and the filtrate was concentrated under reduced pressure. When the concentrate was analyzed (internal standard method) by gas chromatography, 15.9 g (Reaction yield: 81%) of 4-aminotetrahydropyran was found to be formed. Then, 200 ml of n-butyl alcohol and 27.6 g (160.0 mmol) of 47% by weight hydrobromic acid were added to the concentrate, and the resulting mixture was concentrated under reduced pressure to obtain 17.4 g (Isolation yield: 49%) of 4-aminotetrahydropyran hydrobromide with a purity of 99% (areal percentage by gas chromatography) as white crystals.

Physical properties of the 4-aminotetrahydropyran hydrobromide are as follows.

Melting point; 175 to 180° C.

CI-MS (m/e); 102 (M+1-HBr)

$^1$H-NMR (DMSO-$d_6$, δ (ppm)); 1.50 to 1.64 (2H, m), 1.83 to 1.91 (2H, m), 3.20 to 3.6 (3H, m), 3.84 to 3.89 (2H, m), 8.14 (3H, brs)

Example 8

Synthesis of 4-aminotetrahydropyran

To a flask having an inner volume of 100 ml, made of glass and equipped with a stirring device, a thermometer and a reflux condenser were charged 1.0 g (6.49 mmol) of 4-hydrazinotetrahydropyran hydrochloride with a purity of 99% and synthesized in the same manner as in Reference example 2, 3.0 g (0.38 mmol calculated as platinum atom) of 5% by weight platinum/carbon (50% wet product) and 5 ml of ethanol, and the mixture was reacted at 75° C. for 72 hours under hydrogen atmosphere (0.1 MPa). After completion of the reaction, the reaction mixture was cooled to room temperature and filtered, and the filtrate was concentrated under reduced pressure. when the concentrate was analyzed (internal standard method) by gas chromatography, 0.48 g (Reaction yield: 73%) of 4-aminotetrahydropyran was found to be formed.

Example 9

Synthesis of 4-aminotetrahydropyran

To a flask having an inner volume of 100 ml, made of glass and equipped with a stirring device, a thermometer and a reflux condenser were charged 3.0 g (19.5 mmol) of 4-hydrazinotetrahydropyran hydrochloride with a purity of 99% and synthesized in the same manner as in Reference example 2, 600 mg (0.08 mmol calculated as platinum atom) of 5% by weight platinum/carbon (50% wet product), 5 ml of ethanol and 6 ml of water, and the mixture was reacted at 75° C. for 3 hours under hydrogen atmosphere (1.0 MPa). After completion of the reaction, the reaction mixture was cooled to room temperature and filtered, and the filtrate was concentrated under reduced pressure. When the concentrate was analyzed (internal standard method) by gas chromatography, 1.4 g (Reaction yield: 71%) of 4-aminotetrahydropyran was found to be formed.

Example 10

Synthesis of 4-amino-2-methyltetrahydropyran

To a flask having an inner volume of 100 ml, made of glass and equipped with a stirring device, a thermometer and a reflux condenser were charged 1.0 g (5.94 mmol) of 4-hydrazino-2-methyltetrahydropyran hydrochloride with a purity of 99% and synthesized in the same manner as in Example 4(1), 100 mg (0.02 mmol calculated as palladium atom) of 5% by weight palladium/carbon (50% wet product), 2.5 ml of ethanol and 2.5 ml of water, and the mixture was reacted at 75° C. for 24 hours under hydrogen atmosphere (0.1 MPa). After completion of the reaction, the reaction mixture was cooled to room temperature and filtered, and the filtrate was concentrated under reduced pressure. When the concentrate was analyzed (internal standard method) by gas chromatography, 0.59 g (Reaction yield: 86%) of 4-amino-2-methyltetrahydropyran was found to be formed.

Example 11

Synthesis of 4-aminotetrahydropyran hydrochloride

To a flask having an inner volume of 100 ml, made of glass and equipped with a stirring device, a thermometer and a reflux condenser were charged 1.0 g (6.49 mmol) of 4-hydrazinotetrahydropyran hydrochloride with a purity of 99% and synthesized in the same manner as in Reference example 2, 6.2 ml of ethanol, 12 ml (12 mmol) of 1 mol/l aqueous sodium hydroxide solution and 1.5 g (10 mmol) of copper (I) oxide, and the mixture was reacted at 65° C. for 1 hour. After completion of the reaction, the reaction mixture was cooled to room temperature and filtered, and the filtrate was concentrated under reduced pressure. When the concentrate was analyzed (internal standard method) by gas chromatography, 0.47 g (Reaction yield: 50%) of 4-aminotetrahydropyran was found to be formed. Then, 5 ml of n-butyl alcohol and 1 ml (12.0 mmol) of 12 mol/l hydrochloric acid were added to the concentrate, and the resulting mixture was concentrated under reduced pressure to obtain 0.42 g (Isolation yield: 46%) of 4-aminotetrahydropyran hydrochloride with a purity of 98% (areal percentage by gas chromatography) as white crystals.

Physical properties of the 4-aminotetrahydropyran hydrochloride were the same as those in Example 2.

Example 12

Synthesis of 4-aminotetrahydropyran hydrochloride

To a flask having an inner volume of 20 L, made of glass and equipped with a stirring device, a thermometer, a dropping funnel and a reflux condenser were charged 5873 g (115 mol) of 98% aqueous hydrazine solution and 2072 ml of ethanol, and the mixture was heated to 75° C. with stirring. Then, a solution in which 2136 g (11.5 mol) of tetrahydropyranyl-4-methanesulfonate with a purity of 97% had been dissolved in 2072 ml of ethanol was gradually added dropwise to the mixture, and the mixture was reacted at the same temperature for 4 hours with stirring. After completion of the reaction, the mixture was cooled to room temperature to obtain a reaction mixture comprising 4-hydrazinotetrahydropyran as a main product.

Then, to a flask having an inner volume of 20 L, made of glass and equipped with a stirring device, a thermometer, a dropping funnel and a reflux condenser were charged 414.4 g (4.6 mol calculated as nickel atom) of 65% by weight developed Raney nickel and 2072 ml of water, and the mixture was heated up to 60° C. with stirring. Then, the reaction mixture was gradually added dropwise, and the resulting mixture was reacted at 80° C. for 2 hours with stirring. After completion of the reaction, the reaction mixture was cooled up to 40° C., Raney nickel was filtered off, and the filtrate was concentrated under reduced pressure to obtain 818.0 g of the reaction solution containing 4-aminotetrahydropyran as a main product.

To a flask having an inner volume of 20 L, made of glass and equipped with a stirring device, a thermometer, a dropping funnel, a reflux condenser and a distillation device under reduced pressure were charged the above reaction solution, 2072 ml (10.9 mol) of tetraethylenepentamine and 4100 ml of n-butyl alcohol, and the mixture was stirred at 80° C. for 2 hours under reduced pressure. Then, 4-aminotetrahydropyran and n-butyl alcohol were removed by azeotropic distillation under reduced pressure. Thereafter, 4100 ml of n-butyl alcohol was added again, 4-aminotetrahydropyran and n-butyl alcohol were removed by azeotropic distillation under reduced pressure. This operation was repeated to three times to obtain 15000 ml of a distilled solution in total. To the distilled solution was added 575 ml (6.90 mol) of conc. hydrochloric acid, and then, the mixture was concentrated under reduced pressure. To the concentrate was again added 8200 ml of n-butyl alcohol, and water and n-butyl alcohol were removed by azeotropic distillation under reduced pressure. Then, 7460 ml of n-butyl alcohol and 3730 ml of ethanol were added to the residue, and the resulting mixture was once heated up to 115° C. and stirred, then, it was gradually cooled to −5° C. and stirred for 30 minutes. After the filtration, the filtrate was washed with cooled toluene and dried to obtain 788.9 g (Isolation yield based on tetrahydropyranyl-4-methanesulfonate: 49%) of 4-aminotetrahydropyran hydrochloride with a purity of 99% (internal standard method by gas chromatography) as white needle-like crystals.

Physical properties of the 4-aminotetrahydropyran hydrochloride were the same as those in Example 2.

Example 13

Synthesis of 4-amino-2-methyltetrahydropyran hydrochloride

To a flask having an inner volume of 500 ml, made of glass and equipped with a stirring device, a thermometer, a dropping funnel and a reflux condenser were charged 97 ml (1.99 mol) of hydrazine monohydrate and 33 ml of ethanol, and the mixture was heated up to 75° C. with stirring. Then, a solution in which 30.0 g (0.131 mol) of 2-methyltetrahydropyranyl-4-methanesulfonate with a purity of 85% and dissolved in 33 ml of ethanol was gradually added to the mixture dropwise, and the mixture was reacted at the same temperature for 8 hours with stirring. After completion of the reaction, the mixture was cooled up to room temperature to obtain a reaction solution containing 4-hydrazino-2-methyltetrahydropyran as a main product.

Then, to a flask having an inner volume of 500 ml, made of glass and equipped with a stirring device, a thermometer, a dropping funnel, a reflux condenser and a distillation device under reduced pressure were charged 6.0 g (66.4 mmol calculated as nickel atom) of 65% by weight developed Raney nickel, 33 ml of ethanol and 33 ml of water, and the mixture was heated up to 65° C. with stirring. Then, the reaction solution was gradually added dropwise to the mixture, and the mixture was reacted at 65° C. for 2 hours with stirring. After completion of the reaction, the reaction mixture was cooled to room temperature, Raney nickel was filtered off, and the filtrate was concentrated under reduced pressure to obtain a reaction solution containing 4-amino-2-methyltetrahydropyran as a main product.

To the reaction solution were added 30 ml (158.2 mmol) of pentaethylenehexamine and 30 ml of n-butyl alcohol, and the mixture was stirred at 80° C. for 2 hours under reduced pressure. Then, 4-amino-2-methyltetrahydropyran and n-butyl alcohol were removed by azeotropic distillation under reduced pressure. Thereafter, the distilled solution was cooled up to 0° C., 15 ml (180 mmol) of 12 mol/l hydrochloric acid was added thereto, and the resulting mixture was concentrated under reduced pressure to obtain 10.2 g (Isolation yield based on 2-methyltetrahydropyranyl-4-methanesulfonate: 51%) of 4-amino-2-methyltetrahydropyran hydrochloride with a purity of 99% (areal percentage by gas chromatography) as colorless crystals.

Physical properties of the 4-amino-2-methyltetrahydopyran hydrochloride were the same as those in Example 4(2).

Example 14

Synthesis of 4-aminotetrahydropyran methanesulfonate

To a flask having an inner volume of 500 ml, made of glass and equipped with a stirring device, a thermometer, a dropping funnel and a reflux condenser were charged 97 ml (1.99 mol) of hydrazine monohydrate and 33 ml of ethanol, and the mixture was heated up to 75° C. with stirring. Then, a solution in which 30.0 g (0.141 mol) of tetrahydropyranyl-4-methanesulfonate with a purity of 85% had been dissolved in 33 ml of ethanol was gradually added dropwise thereto, and the mixture was reacted at the same temperature for 8 hours with stirring. After completion of the reaction, the mixture was cooled up to room temperature to obtain a reaction solution containing 4-hydrazinotetrahydropyran as a main product.

Then, to a flask having an inner volume of 500 ml, made of glass and equipped with a stirring device, a thermometer, a dropping funnel, a reflux condenser and a distillation device under reduced pressure were charged 6.0 g (66.4 mol calculated as nickel atom) of 65% by weight developed Raney nickel, 33 ml of ethanol and 33 ml of water, and the mixture was heated up to 65° C. with stirring. Then, the above reaction solution was gradually added dropwise to the mixture, and the mixture was reacted at 65° C. for 2 hours with stirring. After completion of the reaction, the reaction mixture was cooled to room temperature, Raney nickel was filtered off, and the filtrate was concentrated under reduced pressure to obtain a reaction solution containing 4-aminotetrahydropyran as a main product.

To the reaction solution were added 30 ml (215.2 mmol) of triethylamine and 30 ml of n-butyl alcohol, the mixture was stirred at room temperature for 1 hour, and precipitated crystals were filtered off. Then, the filtrate was concentrated under reduced pressure to obtain 15.2 g (Isolation yield based on tetrahydropyranyl-4-methanesulfonate: 52%) of 4-aminotetrahydropyran methanesulfonate with a purity of 96% (internal standard method by gas chromatography) as colorless crystals.

Physical properties of the 4-aminotetrahydropyran methanesulfonate were as follows.
Melting point; 204 to 208° C.
CI-MS (m/e); 102 (M+1—$CH_3SO_3H$)
$^1$H-NMR (DMSO-$d_6$, δ (ppm)); 1.45 to 1.60 (2H, m), 1.80 to 1.91 (2H, m), 2.38 (3H, s), 3.15 to 3.36 (3H, m), 3.84 to 3.89 (2H, m), 7.99 (3H, brs)

Example 15

Synthesis of 4-aminotetrahydropyran

To a flask having an inner volume of 100 ml, made of glass and equipped with a stirring device, a thermometer, a dropping funnel and a reflux condenser were charged 19 ml (0.39 mol) of hydrazine monohydrate and 19 ml of ethanol, and the mixture was heated up to 75° C. with stirring. Then, a solution in which 10.0 g (0.039 mol) of tetrahydropyranyl-4-p-toluenesulfonate with a purity of 100% had been dissolved in 19 ml of ethanol was gradually added dropwise to the mixture, and the mixture was reacted at the same temperature for 8 hours with stirring. After completion of the reaction, the mixture was cooled up to room temperature to obtain a reaction solution containing 4-hydrazinotetrahydropyran as a main product.

Then, to a flask having an inner volume of 100 ml, made of glass and equipped with a stirring device, a thermometer, a dropping funnel, a reflux condenser and a distillation device under reduced pressure were charged 2.6 g (28.8 mmol calculated as nickel atom) of 65% by weight developed Raney nickel, 19 ml of ethanol and 19 ml of water, and the mixture was heated up to 65° C. with stirring. Then, the above reaction solution was gradually added dropwise thereto, and the resulting mixture was reacted at 65° C. for 2 hours with stirring. After completion of the reaction, the reaction mixture was cooled to room temperature, Raney nickel was filtered off, and when the filtrate was analyzed (internal standard method) by gas chromatography, 1.2 g (Isolation yield based on tetrahydropyranyl-4-p-toluenesulfonate: 30%) of 4-aminotetrahydropyran was found to be formed.

Example 16

Synthesis of 2-methyltetrahydropyran-4-methanesulfonate

To 100 ml of a flask made of glass and equipped with a stirring device, a thermometer, a dropping funnel and a reflux condenser were charged 5.00 g (69.3 mmol) of 3-buten-1-ol, 3.67 g (83.4 mmol in terms of acetaldehyde) of paraldehyde (acetaldehyde trimer) and 50 ml of toluene, under nitrogen atmosphere, 7.99 g (83.1 mmol) of methanesulfonic acid was gradually added dropwise to the mixture with stirring, and reacted at 55° C. for 4 hours. After completion of the reaction, to the obtained mixture was added 50 ml of an aqueous saturated sodium chloride solution, and extracted with 50 ml of ethyl acetate. Then, the extract was washed with 1 mol/l of an aqueous sodium hydroxide solution and an aqueous saturated sodium chloride solution, and dried over anhydrous magnesium sulfate. After filtration, the filtrate was concentrated under reduced pressure, and purified by silica gel column chromatography (eluent; hexane:ethyl acetate=10:1→3:1) to obtain 8.79 g (Isolation yield: 65%) of 2-methyltetramethaneulfonate-4-methanesulfonate as pale yellowish liquid.

2-Methyltetrahydropyran-4-methanesulfonate is a novel compound shown by the following physical properties.

CI-MS (m/e); 195 (M+1)

$^1$H-NMR (CDCl$_3$, δ (ppm)); 1.23 (3H, d, J=6.0 Hz), 1.44 to 1.56 (1H, m), 1.76 to 1.81 (1H, m), 2.02 to 2.16 (2H, m), 3.03 (3H, s), 3.45 to 3.51 (2H, m), 4.00 to 4.06 (1H, m), 4.75 to 4.83 (1H, m)

UTILIZABILITY IN INDUSTRY

According to the present invention, an industrially suitable process for preparing 4-aminotetrahydropyran compound and an acid salt thereof which can prepare 4-aminotetrahydropyran compound and an acid salt thereof without requiring complicated operations with a simple and easy method can be provided. Also, according to the present invention, industrially suitable 2-substituted tetrahydropyranyl-4-sulfonate and a process for preparing the same which can prepare 2-substituted tetrahydropyranyl-4-sulfonate under mild conditions and simple and easy method with a high yield can be provided.

The invention claimed is:

1. A process for preparing a 4-aminotetrahydropyran compound represented by the formula (1):

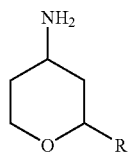

(1)

wherein R represents a hydrogen atom or a hydrocarbon group,
or an acid salt thereof,
which comprises subjecting a 4-hydrazinotetrahydropyran compound represented by the formula (2):

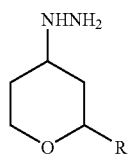

(2)

wherein R has the same meaning as defined above,
or an acid salt thereof
to decomposition reaction in the presence of at least one compound selected from Raney nickel, a noble metal catalyst and a metal oxide.

2. The process for preparing a 4-aminotetrahydropyran compound or an acid salt thereof according to claim 1, wherein the noble metal catalyst is a catalyst containing at least one of palladium and platinum.

3. The process for preparing a 4-aminotetrahydropyran compound or an acid salt thereof according to claim 1, wherein the metal oxide is copper (I) oxide or copper (II) oxide.

4. The process for preparing a 4-aminotetrahydropyran compound or an acid salt thereof according to claim 1, wherein the reaction is carried out in a solvent.

5. The process for preparing a 4-aminotetrahydropyran compound or an acid salt thereof according to claim 4, wherein the solvent is water, an alcohol, or a mixed solvent thereof.

6. The process for preparing a 4-aminotetrahydropyran compound or an acid salt thereof according to claim 1, wherein the compound represented by the formula (2) is a compound obtained by reacting a 4-substituted tetrahydropyran compound represented by the formula (3):

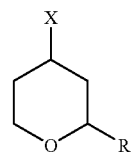

(3)

wherein R has the same meaning as defined above, and X represents a leaving group, with a hydrazine.

7. A process for preparing a 4-aminotetrahydropyran compound or an acid salt thereof, which comprises
(A) the first step of reacting a 4-substituted tetrahydropyran compound represented by the formula (3):

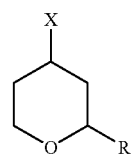

(3)

wherein R represents a hydrogen atom or a hydrocarbon group, and X represents a leaving group,
with a hydrazine to prepare a 4-hydrazinotetrahydropyran compound represented by the formula (2):

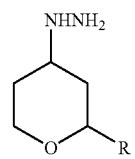

(2)

wherein R has the same meaning as defined above,
or an acid salt thereof,
(B) then, A second step of decomposing the 4-hydrazinotetrahydropyran compound or an acid salt thereof in the reaction mixture in the presence of at least one compound selected from Raney nickel, a noble metal catalyst and a metal oxide to prepare a 4-aminotetrahydropyran compound represented by the formula (1):

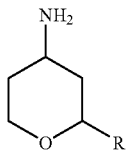
(1)

wherein R has the same meaning as defined above.

8. The process for preparing a 4-aminotetrahydropyran compound or an acid salt thereof according to claim 7, wherein the first step is carried out in a solvent.

9. The process for preparing a 4-aminotetrahydropyran compound or an acid salt thereof according to claim 7, wherein the solvent used in the first step is an alcohol derivative.

10. The process for preparing a 4-aminotetrahydropyran compound or an acid salt thereof according to claim 7, wherein the second step is carried out in a solvent.

11. The process for preparing a 4-aminotetrahydropyran compound or an acid salt thereof according to claim 10, wherein the solvent used in the second step is water, an alcohol or a mixture thereof.

12. The process for preparing a 4-aminotetrahydropyran compound or an acid salt thereof according to claim 7, wherein an amine is used at the time of removing the Raney nickel from the reaction mixture after completion of the reaction at the second step.

* * * * *